(12) United States Patent
Stahmann et al.

(10) Patent No.: US 7,967,756 B2
(45) Date of Patent: Jun. 28, 2011

(54) RESPIRATORY THERAPY CONTROL BASED ON CARDIAC CYCLE

(75) Inventors: Jeffrey E. Stahmann, Ramsey, MN (US); Jesse W. Hartley, Lino Lakes, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 804 days.

(21) Appl. No.: 10/943,074

(22) Filed: Sep. 15, 2004

(65) Prior Publication Data

US 2005/0109339 A1 May 26, 2005

Related U.S. Application Data

(60) Provisional application No. 60/504,073, filed on Sep. 18, 2003.

(51) Int. Cl.
*A61N 1/365* (2006.01)
*A61B 5/08* (2006.01)

(52) U.S. Cl. .......................... 600/484; 607/20; 600/529

(58) Field of Classification Search .................. 600/547, 600/508, 509, 529
See application file for complete search history.

(56) References Cited

U.S. PATENT DOCUMENTS

| | | |
|---|---|---|
| 4,312,734 A | 1/1982 | Nichols |
| 4,365,636 A | 12/1982 | Barker |
| 4,390,405 A | 6/1983 | Hahn et al. |
| 4,562,841 A | 1/1986 | Brockway et al. |
| 4,777,962 A | 10/1988 | Watson et al. |
| 4,802,485 A | 2/1989 | Bowers et al. |
| 4,813,427 A | 3/1989 | Schlaefke et al. |
| 4,830,008 A | 5/1989 | Meer |
| 4,875,477 A | 10/1989 | Waschke et al. |
| 4,928,674 A | 5/1990 | Halperin et al. |
| 4,928,688 A | 5/1990 | Mower |
| 4,961,423 A | 10/1990 | Canducci |
| 4,982,738 A | 1/1991 | Griebel |
| 5,003,976 A | 4/1991 | Alt |
| 5,036,849 A | 8/1991 | Hauck et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,174,287 A | 12/1992 | Kallok et al. |

(Continued)

FOREIGN PATENT DOCUMENTS

EP 0940155 A 8/1999

(Continued)

OTHER PUBLICATIONS

Pinsky et al., *Hemodynamic Effect of Cardiac Cycle-Specific Increases in Intrathoracic Pressure*, 6 J. Appl. Physiol. 604-612 (1986). (Abstract only).

(Continued)

*Primary Examiner* — Carl H. Layno
*Assistant Examiner* — Jon-Eric C. Morales
(74) *Attorney, Agent, or Firm* — Hollingsworth & Funk, LLC

(57) ABSTRACT

Methods and systems involve adjusting respiratory therapy based on cardiac cycle phase. A parameter indicative of cardiac cycle is sensed and the respiratory therapy is adjusted based on cardiac cycle phase. Modulation of respiratory therapy pressure reinforces the pumping action of the heart and results in increased cardiac output with decreased expenditure of myocardial energy output.

23 Claims, 11 Drawing Sheets

U.S. PATENT DOCUMENTS

| | | |
|---|---|---|
| 5,183,038 A | 2/1993 | Hoffman et al. |
| 5,187,657 A | 2/1993 | Forbes |
| 5,199,424 A | 4/1993 | Sullivan et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan et al. |
| 5,259,373 A | 11/1993 | Gruenke et al. |
| 5,284,136 A | 2/1994 | Hauck et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A * | 10/1994 | Miles ............ 128/204.23 |
| 5,360,442 A | 11/1994 | Dahl et al. |
| 5,366,496 A | 11/1994 | Dahl et al. |
| 5,376,476 A | 12/1994 | Eylon |
| 5,377,671 A * | 1/1995 | Biondi et al. ............ 128/204.23 |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,398,682 A | 3/1995 | Lynn |
| 5,411,031 A | 5/1995 | Yomtov |
| 5,466,245 A | 11/1995 | Heemels et al. |
| 5,483,969 A | 1/1996 | Testerman et al. |
| 5,485,851 A | 1/1996 | Erickson |
| 5,517,983 A | 5/1996 | Deighan et al. |
| 5,522,382 A | 6/1996 | Sullivan et al. |
| 5,522,862 A | 6/1996 | Testerman et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,554,177 A * | 9/1996 | Kieval et al. ............ 607/17 |
| 5,590,648 A | 1/1997 | Mitchell et al. |
| 5,591,216 A | 1/1997 | Testerman et al. |
| 5,593,431 A | 1/1997 | Sheldon |
| 5,603,732 A | 2/1997 | Dahl et al. |
| 5,605,151 A | 2/1997 | Lynn |
| 5,645,570 A | 7/1997 | Corbucci |
| 5,693,000 A | 12/1997 | Crosby et al. |
| 5,701,894 A | 12/1997 | Cherry et al. |
| 5,715,812 A | 2/1998 | Deighan et al. |
| 5,738,102 A | 4/1998 | Lemelson |
| 5,740,797 A * | 4/1998 | Dickson ............ 128/204.28 |
| 5,800,470 A | 9/1998 | Stein et al. |
| 5,814,087 A | 9/1998 | Renirie |
| 5,826,579 A | 10/1998 | Remmers et al. |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,911,218 A | 6/1999 | DiMarco |
| 5,916,243 A | 6/1999 | KenKnight et al. |
| 5,944,680 A | 8/1999 | Christopherson et al. |
| 5,964,778 A | 10/1999 | Fugoso et al. |
| 5,964,788 A | 10/1999 | Greenhut |
| 5,974,340 A * | 10/1999 | Kadhiresan ............ 607/18 |
| 5,974,349 A | 10/1999 | Levine |
| 6,015,388 A | 1/2000 | Sackner et al. |
| 6,026,320 A | 2/2000 | Carlson et al. |
| 6,044,297 A | 3/2000 | Sheldon et al. |
| 6,044,298 A | 3/2000 | Salo et al. |
| 6,045,513 A | 4/2000 | Stone et al. |
| 6,047,203 A | 4/2000 | Sacker et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,105,575 A | 8/2000 | Estes et al. |
| 6,120,441 A | 9/2000 | Griebel |
| 6,126,611 A * | 10/2000 | Bourgeois et al. ............ 600/529 |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,155,976 A | 12/2000 | Sackner et al. |
| 6,161,042 A | 12/2000 | Hartley et al. |
| 6,165,155 A | 12/2000 | Jacobsen et al. |
| 6,168,568 B1 | 1/2001 | Gavriely |
| 6,190,326 B1 | 2/2001 | McKinnon et al. |
| 6,221,011 B1 | 4/2001 | Bardy |
| 6,236,873 B1 | 5/2001 | Holmstrom |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,261,238 B1 | 7/2001 | Gavriely |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,287,264 B1 | 9/2001 | Hoffman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Harley et al. |
| 6,351,670 B1 | 2/2002 | Kroll |
| 6,353,759 B1 | 3/2002 | Harley et al. |
| 6,357,444 B1 | 3/2002 | Parker |
| 6,358,203 B2 | 3/2002 | Bardy |
| 6,361,522 B1 | 3/2002 | Scheiner et al. |
| 6,363,270 B1 | 3/2002 | Colla et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,375,623 B1 | 4/2002 | Gavriely |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,411,848 B2 | 6/2002 | Kramer et al. |
| 6,415,183 B1 | 7/2002 | Scheiner et al. |
| 6,424,865 B1 | 7/2002 | Ding |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,449,503 B1 | 9/2002 | Hsu |
| 6,459,929 B1 | 10/2002 | Hopper et al. |
| 6,463,326 B1 | 10/2002 | Hartley et al. |
| 6,468,219 B1 | 10/2002 | Njemanze |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,572,543 B1 | 6/2003 | Christopherson et al. |
| 6,574,507 B1 | 6/2003 | Bonnet |
| 6,589,188 B1 | 7/2003 | Street et al. |
| 6,597,951 B2 | 7/2003 | Kramer et al. |
| 6,600,949 B1 | 7/2003 | Turcott |
| 6,606,993 B1 | 8/2003 | Wiesmann et al. |
| 6,641,542 B2 | 11/2003 | Cho et al. |
| 6,658,292 B2 | 12/2003 | Kroll et al. |
| 6,723,055 B2 | 4/2004 | Hoffman |
| 6,741,885 B1 | 5/2004 | Park et al. |
| 6,752,765 B1 | 6/2004 | Jensen et al. |
| 6,773,404 B2 | 8/2004 | Poezevera et al. |
| 6,810,287 B2 | 10/2004 | Zhu et al. |
| 6,811,538 B2 * | 11/2004 | Westbrook et al. ............ 600/529 |
| 6,876,881 B2 | 4/2005 | Baumann et al. |
| 6,881,192 B1 | 4/2005 | Park |
| 6,904,320 B2 * | 6/2005 | Park et al. ............ 607/17 |
| 6,907,288 B2 | 6/2005 | Daum |
| 6,928,324 B2 * | 8/2005 | Park et al. ............ 607/20 |
| 7,025,730 B2 * | 4/2006 | Cho et al. ............ 600/529 |

| | | | |
|---|---|---|---|
| 7,092,755 B2 * | 8/2006 | Florio | 607/9 |
| 7,189,204 B2 | 3/2007 | Ni et al. | |
| 7,225,013 B2 | 5/2007 | Geva et al. | |
| 7,252,640 B2 | 8/2007 | Ni et al. | |
| 7,258,670 B2 | 8/2007 | Bardy | |
| 7,308,311 B2 | 12/2007 | Sorensen et al. | |
| 7,396,333 B2 | 7/2008 | Stahmann et al. | |
| 7,438,686 B2 | 10/2008 | Cho et al. | |
| 7,486,991 B2 | 2/2009 | Libbus et al. | |
| 7,509,166 B2 | 3/2009 | Libbus | |
| 2002/0193697 A1 * | 12/2002 | Cho et al. | 600/529 |
| 2002/0193839 A1 | 12/2002 | Cho et al. | |
| 2003/0023184 A1 | 1/2003 | Pitts-Crick et al. | |
| 2003/0055461 A1 | 3/2003 | Girouard et al. | |
| 2003/0100925 A1 | 5/2003 | Pape et al. | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0195571 A1 * | 10/2003 | Burnes et al. | 607/9 |
| 2003/0199945 A1 | 10/2003 | Ciulla | |
| 2003/0204213 A1 | 10/2003 | Jensen et al. | |
| 2004/0002742 A1 | 1/2004 | Florio | |
| 2004/0030362 A1 | 2/2004 | Hill et al. | |
| 2004/0059240 A1 | 3/2004 | Cho et al. | |
| 2004/0088015 A1 * | 5/2004 | Casavant et al. | 607/14 |
| 2004/0088027 A1 * | 5/2004 | Burnes et al. | 607/60 |
| 2004/0133079 A1 | 7/2004 | Mazar et al. | |
| 2004/0138719 A1 * | 7/2004 | Cho et al. | 607/42 |
| 2004/0186523 A1 * | 9/2004 | Florio | 607/17 |
| 2005/0039745 A1 | 2/2005 | Stahmann et al. | |
| 2005/0043652 A1 | 2/2005 | Lovett et al. | |
| 2005/0043772 A1 | 2/2005 | Stahmann et al. | |
| 2007/0149860 A1 | 6/2007 | Lynn et al. | |
| 2007/0161873 A1 | 7/2007 | Ni et al. | |
| 2007/0282215 A1 | 12/2007 | Ni et al. | |

FOREIGN PATENT DOCUMENTS

| | | |
|---|---|---|
| EP | 0940155 | 9/1999 |
| EP | 1172125 | 1/2002 |
| JP | 2002519161 | 7/2002 |
| WO | 99/04841 | 2/1999 |
| WO | WO0001438 | 1/2000 |
| WO | WO0017615 | 3/2000 |
| WO | WO0240096 | 5/2002 |
| WO | 02/087696 | 7/2002 |
| WO | WO02075744 | 9/2002 |
| WO | WO03075744 | 9/2003 |
| WO | WO2004062485 | 7/2004 |
| WO | WO2005028029 | 3/2005 |

OTHER PUBLICATIONS

Bradley et al, *Cardiac Output Response to Continuous Positive Airway Pressure in Congestive Heart Failure*, 145 Am. Rev. Respir. Dis. 377-382 (1992). (Abstract only).

Hanson et al., *Cardiac Gated Ventilation*, 2433 SPIE 303-308 (1995).

Scharf, *Effects of Continuous Positive Airway Pressure on Cardiac Output in Experimental Heart Failure*, 19 Sleep S240-2 (1996). (Abstract only).

De Hoyos et al., *Haemodynamic Effects of Continuous Positive Airway Pressure in Humans With Normal and Impaired Left Ventricular Function*, 88 Clin. Sci. (Lond). 173-8 (1995). (Abstract only).

Baratz et al., *Effect of Nasal Continuous Positive Airway Pressure on Cardiac Output and Oxygen Delivery in Patients With Congestive Heart Failure*, 102 Chest. 397-401(1992). Abstract only.

Mehta et al., *Effects of Continuous Positive Airway Pressure on Cardiac Volumes in Patients With Ischemic and Dilated Cardiomyopathy*, 161 Am. J. Respir. Crit. Care Med. 128-134 (2000).

Weber et al. *Effects of CPAP and BIPAP on stroke volume in patients with obstructive sleep apnea syndrome*. Pneumolgie Mar. 1995;49(3):233-5. Abstract translation only.

Lenique et al., *Ventilatory and Hemodynamic Effects of Continuous Positive Airway Pressure in Left Heart Failure*, 155 Am. J. Respir. Crit. Care Med. 500-505 (1997). (Abstract only).

Pinsky et al., *Augmentation of Cardiac Function by Elevation of Intrathoracic Pressure*, 54 J. Appl. Physiol. 950-955 (1983). (Abstract only).

Naughton et al., *Effects of Continuous Positive Airway Pressure on Intrathoracic and Left Ventricular Transmural Pressure in Congestive Heart Failure*, 91 Circulation 1725-1731 (1995).

Rasanen et al., *Acute Myocardial Infarction Complicated by Left Ventricular Dysfunction and Respiratory Failure. The Effects of Continuous Positive Airway Pressure*, 87 Chest 158-62 (1985). (Abstract only).

Calvin et al., *Positive End-Expiratory Pressure (PEEP) Does Not Depress Left Ventricular Function in Patients With Pulmonary Edema*, 124 Am. Rev. Respir. Dis. 121-128 (1981). (Abstract only).

Potkin et al., *Effect of positive end-expiratory pressure on right and left ventricular function in patients with the adult respiratory distress syndrome*, 135 Am. Rev. Respir. Dis. 307-311 (1987). (Abstract only).

Buda et al., *Effect of Intrathoracic Pressure on Left Ventricular Performance*, 301 Engl. J. Med. 453-459 (1979). (Abstract only).

Pinsky et al., *Cardiac Augmentation by Phasic High Intrathoracic Pressure Support in Man*, 84 Chest 370-375 (1983). (Abstract only).

Kaye et al., *Acute Effects of Continuous Positive Airway Pressure on Cardiac Sympathetic Tone in Congestive Heart Failure*, 103 Circulation 2336-24338 (2001).

Laude et al., *Effects of Breathing Pattern on Blood Pressure and Heart Rate Oscillations in Humans*, 20 Clin. Exp. Pharmol. Phisiol 619, 625 (1993). Abstract only.

Giardino et al., *Respiratory Sinus Arrhythmia is Associated with the Efficiency of Pulmonary Gas Exchange in Healthy Humans*, 284 Am. J. Physiol. H1585-1591 (2003). (Abstract only).

Altshule et al., The Effect of Position on Periodic Breathing in Chronic Cardiac Decomposition, New Eng. Journal of Med., vol. 259, No. 22, pp. 1064-1066, Nov. 27, 1958.

Balaban et al., *Feasibility of Screening for Sleep Apnea Using Pacemaker Impedance Sensor*, NASPE (2001).

Bradley et al., *Pathophysiologic and Therapeutic Implications of Sleep Apnea in Congestive Heart Failure*, 3 J. Cardiac Failure 223-240 (1996). Abstract only.

Bradley et al., *Sleep Apnea and Heart Failure, Park I: Obstructive Sleep Apnea*, 107 Circulation 1671-1678 (2003).

Dark et al., Breathing Pattern Abnormalities and Arterial Oxygen Desaturation During Sleep in the Congestive Heart Failure Syndrome, Chest, Jun. 1987, 6:833-6.

Garrigue et al., *Night Atrial Overdrive with DDD Pacing: a New Therapy for Sleep Apnea Syndrome*, NASPE (2000).

Garrigue et al., *Night Atrial Overdrive with DDD Pacing Results in a Significant Reduction of Sleep Apnea Episodes and QOL Improvement in Heart Failure Patients*, NASPE (2001).

Garrigue et al., *Benefit of Atrial Pacing in Sleep Apnea Syndrome*, 346 N. Engl. J. Med. 404-412 (2002).

Hilton et al., *Evaluation of Frequency and Time-frequency Spectral Analysis of Heart Rate Variability as a Diagnostic Marker of the Sleep Apnea Syndrome*, 37 Med. Biol. Eng. Comput. 760-769 (1999).

Hoffman et al., Cheyne-Stokes Respiration in Patients Recovering from Acute Cardiogenic Pulmonary Edema, Chest 1990, 97:410-12.

Holger Steltner et al., *Diagnosis of Sleep Apnea by Automatic Analysis of Nasal Pressure and Forced Oscillation Impedance*. Am. Journal Respiratory Critical Care Medicine, vol. 165, pp. 940-944 (2002).

Javaheri, *A Mechanism of Central Sleep Apnea in Patients With Heart Failure*, 341 N. Engl. J. Med. 949-954 (1999).

Javaheri et al., *Sleep Apnea in 81 Ambulatory Male Patients with Stable Heart Failure: Types and Their Prevalences, Consequences, and Presentations*, 97 Circulation 2154-2159 (1998).

Junyu et al., Posture Detection Algorithm Using Multi Axis DC-Accelerometer, Pace vol. 22, Apr. 1999.

Lugaresi et al., *Snoring*, 39 Electroencephalogr. Clin. Neurophysiol. 59-64 (1975).

Mansfield, D. et al., *Effects of Continuous Positive Airway Pressure on Lung Function in Patients with Chronic Obstructive Pulmonary Disease and Sleep Disordered Breathing*, Respirology 365-70 (1999). Abstract only.

Olusola et al., *Nightcap: Laboratory and home-based evaluation of a portable sleep monitor*, 32 Psychophysiology, 32-98 (1995). Abstract only.

Reddel et al., *Analysis of Adherence to Peak Flow Monitoring When Recording of Data is Electronic*, BMJ 146-147 (2002).

Rees et al., Paroxysmal Nocturnal Dyspnoea and Periodic Respiration, The Lancet, Dec. 22-29, 1979, pp. 1315-1317. Abstract Only.

Roche et al., *Screening of Obstructive Sleep Apnea Syndrome by Heart Rate Variability Analysis*, 100 Circulation 1411-1455 (1999).

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Vanninen et al., *Cardiac Sympathovagal Balance During Sleep Apnea Episodes*, 16 Clin. Physiol. 209-216 (1996).

Verrier et al., *Sleep, dreams, and sudden death: the case for sleep as an autonomic stress test for the heart*, 31 Cardiovascular Research 181-211 (1996).

Verrier et al., *Sleep Related Cardiovascular Risk: New Home-Based Monitoring Technology for Improved Diagnosis and Therapy*, 2 A.N.E. 158-175 (1997).

Waldemark et al., *Detection of Apnea using Short Window FFT Technique and Artificial Neural Network*, 3390 SPIE International Society for Optical Engineering 122-133 (1998). Abstract only.

Young et al., *The Occurrence of Sleep-Disordered Breathing Among Middle Aged Adults*, N. Engl. J. Med. 1230-1235 (1993).

Weber et al. Effects of CPAP and BIPAP on stroke volume in patients with obstructive sleep apnea syndrome. Pneumolgie Mar. 1995;49(3):233-5. Abstract translation only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999).

Office Action dated Dec. 19, 2006 from U.S. Appl. No. 10/943,070, 6 pages.

Office Action Response submitted Apr. 23, 2007 to office action dated Dec. 19, 2006 from U.S. Appl. No. 10/943,070, 12 pages.

Notice of Allowance dated Jul. 12, 2007 from U.S. Appl. No. 10/943,070, 7 pages.

Office Action dated May 9, 2007 from European Application No. 04784602.7, 3 pages.

Office Action dated Jan. 10, 2008 from European Application No. 04784602.7, 3 pages.

Office Action Response dated Apr. 17, 2008 from European Application No. 04784602.7, 10 pages.

International Search Report dated Dec. 22, 2004 from PCT Application No. PCT/US2004/030787, 8 pages.

International Search Report dated Jul. 26, 2010 from European Application No. 08075738.8, 4 pages.

\* cited by examiner

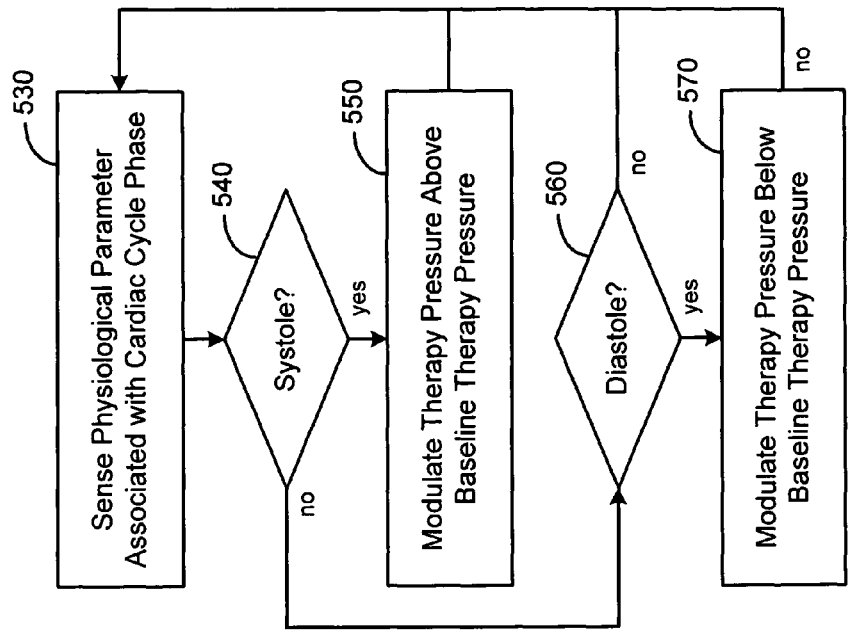
Figure 5B
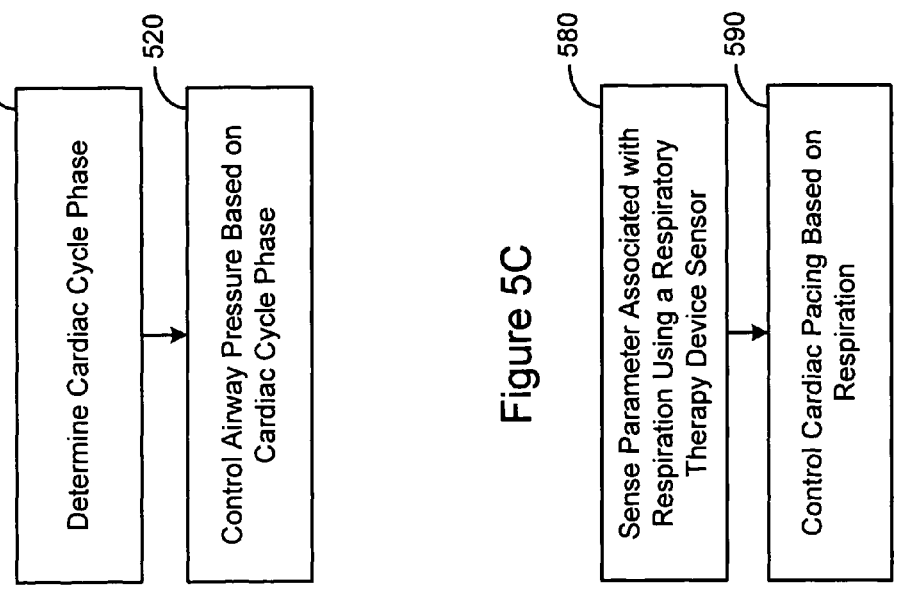
Figure 5A
Figure 5C

US 7,967,756 B2

RESPIRATORY THERAPY CONTROL BASED ON CARDIAC CYCLE

RELATED PATENT DOCUMENTS

This application claims the benefit of Provisional Patent Application Ser. No. 60/504,073, filed on Sep. 18, 2003 and now abandoned, to which priority is claimed pursuant to 35 U.S.C. §119(e) and which is hereby incorporated herein by reference.

FIELD OF THE INVENTION

The present invention relates generally to controlling respiration therapy.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term prognosis as well as the quality of life can be improved if blood pressure and hypertension are reduced. Many patients who suffer from hypertension do not respond to treatment, such as treatments related to lifestyle changes and hypertension drugs.

Effective approaches to treating cardiovascular disorders are needed. The present invention fulfills these and other needs, and addresses other deficiencies of prior art implementations and techniques.

SUMMARY OF THE INVENTION

Various embodiments of present invention involve methods and systems for matching intrathoracic pressure with cardiac cycle phase. One embodiment of the invention involves a method for delivering airway pressure to a patient. The method includes determining the cardiac cycle phase and controlling the airway pressure based on the cardiac cycle phase. Controlling the airway pressure is performed at least in part implantably.

In accordance with another embodiment of the invention, a therapy control system includes a detector system configured to determine cardiac cycle phase and control unit coupled to the detector system. The control unit is configured to control airway pressure based on the cardiac cycle phase. The control unit includes at least one implantable component.

In yet another embodiment of the invention, a method for controlling airway pressure comprises delivering cardiac pacing pulses to a patient and controlling airway pressure delivered to the patient based on the delivery of the cardiac pacing pulses.

A further embodiment of the invention involves a medical system is configured to control airway pressure delivered to a patient. The medical system includes a pulse generator configured to deliver cardiac pacing pulses to a patient's heart and control circuitry coupled to the pulse generator. The control unit configured to control airway pressure delivered to the patient based on the delivery of the cardiac pacing pulses.

Yet a further embodiment involves a method of delivering and external respiratory therapy to a patient. The external respiratory therapy is delivered to a patient to treat disordered breathing. The cardiac cycle phase of the patient is determined. The delivery of the external respiratory therapy is controlled based on the cardiac cycle phase.

In another embodiment of the invention, a medical system controls delivery of a patient-external respiratory therapy based on cardiac cycle phase. The medical system includes a respiratory therapy unit configured to deliver a patient-external respiratory therapy to a patient to treat disordered breathing. The system also includes detector circuitry configured to determine cardiac cycle phase. A control unit is coupled to the detector system and the respiratory therapy unit. The control unit is configured to control delivery of the respiratory therapy based on the cardiac cycle phase.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 5A and 5B are flowcharts of methods of modulating airway pressure based on cardiac cycle phase in accordance with embodiments of the invention;

FIG. 5C is a flowchart of a method for controlling cardiac pacing based on respiration in accordance with embodiments of the invention.

Figure 1A:
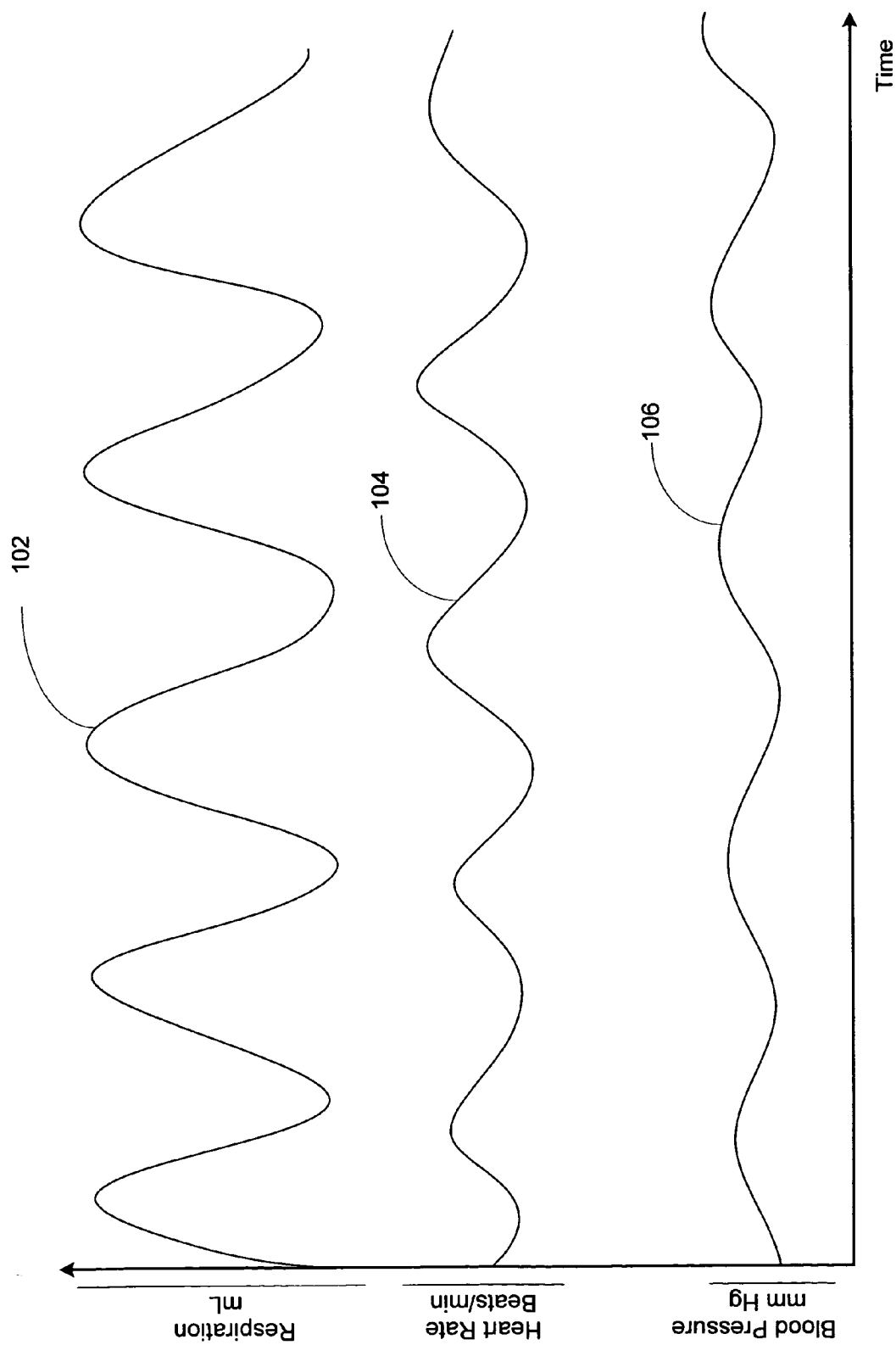
FIG. 1A is a graph illustrating the variation of heart rate and blood pressure with respiration cycles.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Under healthy conditions, heart rate and blood pressure vary with respiration. The heart rate varies in response to autonomic as well as other regulatory inputs to the sinoatrial node (SA). FIG. 1 is a graph comparing respiration 102, blood pressure 106, and heart rate 104 in a healthy individual. Modulation of heart rate with respiration is known as respiratory sinus arrhythmia (RSA). The rate variations of RSA have been found to be important to survival. Individuals without RSA have higher rates of overall mortality than those with RSA.

Respiratory sinus arrhythmia has a role in increasing the efficiency of the cardiovascular system. In many patients with cardiovascular disease or heart failure, RSA is attenuated or absent. Studies have shown that RSA improves pulmonary gas exchange and circulatory efficiency. Mimicking RSA behavior using a cardiac pacemaker enhances cardiac function over fixed pacing.

Some patients suffer from multiple disorders affecting the cardiac and pulmonary systems. For example, patients suffering from congestive heart failure (CHF) may experience disordered breathing as well as a decrease in the pumping action of the heart. In some cases, patients receive therapy from multiple units to improve cardiac and respiratory functioning. For example, a patient may receive treatment for disordered breathing from a patient-external respiratory therapy unit and the patient may receive cardiac resynchronization pacing therapy from a patient-internal cardiac rhythm management (CRM) system.

Various aspects of the invention are directed to coordinated use of multiple therapy devices to increase cardiopulmonary functioning. Some embodiments of the invention utilize information acquired by sensors of a respiratory therapy device to control cardiac pacing based on the interactions of cardiac and pulmonary systems associated with RSA. The cardiac pacing rate may be modulated by respiration to mimic RSA.

Other embodiments of the invention modulate intrathoracic pressure based on cardiac cycle phase. In these embodiments, although the cause/effect relationship of RSA is reversed, the cardiovascular system may benefit from similar efficiencies as RSA because intrathoracic pressure is matched to cardiac cycle.

Methods, devices, and systems in accordance with the present invention may incorporate one or more of the features, structures, methods, or combinations thereof described herein below. For example, a medical system may be implemented to include one or more of the features and/or processes described below. It is intended that such a method, device, or system need not include all of the features and functions described herein, but may be implemented to include one or more selected features and functions that provide unique structures and/or functionality.

Figure 1B:
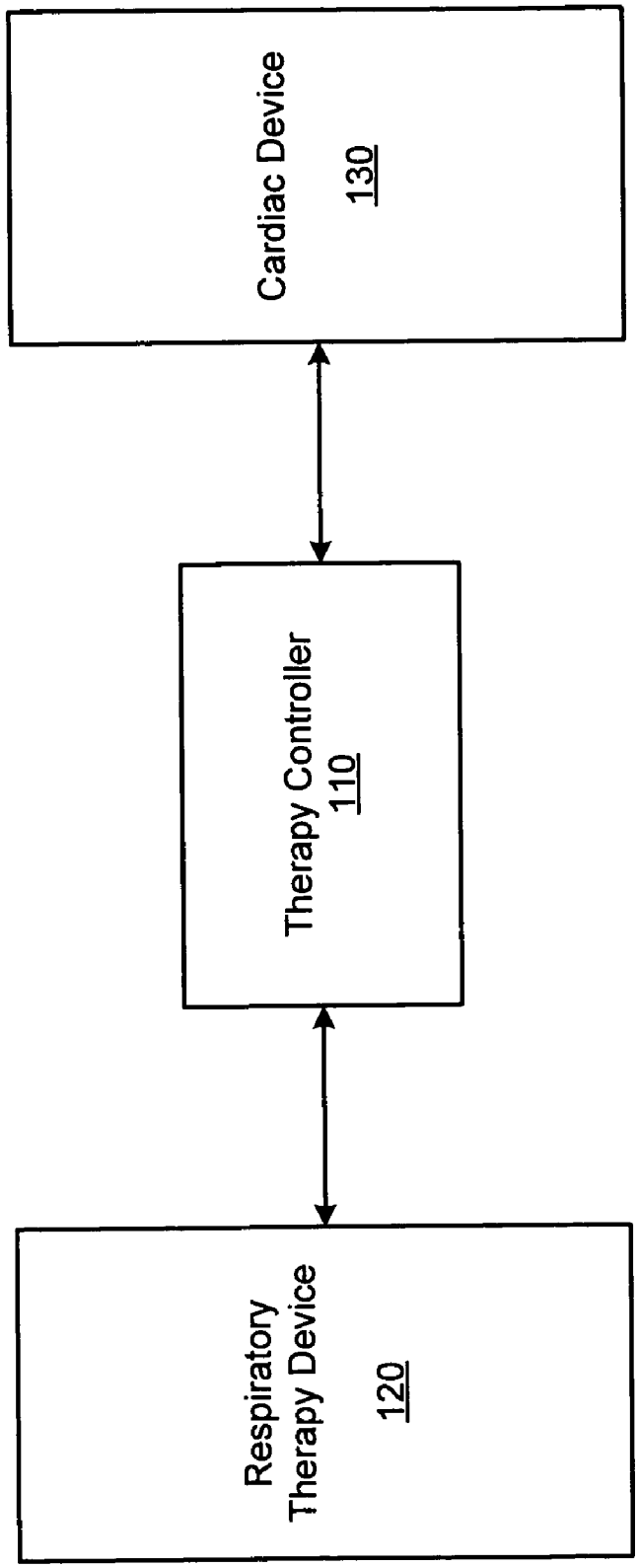
FIG. 1B is a block diagram illustrating a medical system that may be used to coordinate multiple therapy devices to provide therapy for increasing cardiopulmonary functioning in accordance with embodiments of the invention.

FIG. 1B is a block diagram illustrating a medical system that may be used to coordinate multiple therapy devices to provide therapy for increasing cardiopulmonary functioning in accordance with embodiments of the invention. The system includes a therapy controller 110 coupled to a respiratory therapy unit 120 and a cardiac device 130. According to some aspects of the invention, the therapy controller may control the cardiac device to adjust cardiac pacing based on respiration information acquired from sensors of the respiratory therapy system. The therapy controller may modulate cardiac pacing rate based on respiration cycle information acquired from the sensors of the respiratory therapy unit. Methods and systems for controlling cardiac pacing rate based on respiration, aspects of which may be incorporated into embodiments of the invention described herein, are discussed in U.S. Pat. No. 5,964,788, which is incorporated herein by reference.

According to other aspects of the invention, the therapy controller controls airway pressure delivered by the respiratory therapy device based on cardiac cycle phase. In some embodiments, cardiac cycle phase information may be acquired from physiological sensors. In other embodiments, cardiac cycle phase may be determined based on cardiac pacing information. In some embodiments, cardiac cycle phase may be determined based on both cardiac pacing information and on sensed physiological parameters. The therapy controller 110 may control the respiratory therapy device to modulate intrathoracic pressure above and below a baseline pressure in synchrony with cardiac cycles.

In some implementations, the therapy controller may be a component of the respiratory therapy device with the therapy controller circuitry disposed within the controller unit, typically a bedside unit, of the respiratory therapy device. In other implementations, the therapy controller may be implantable. For example, the therapy controller may be disposed within a housing of an implantable cardiac therapy device. In yet other embodiments the therapy controller is separate from the cardiac device and the respiratory therapy device.

Figure 2A:
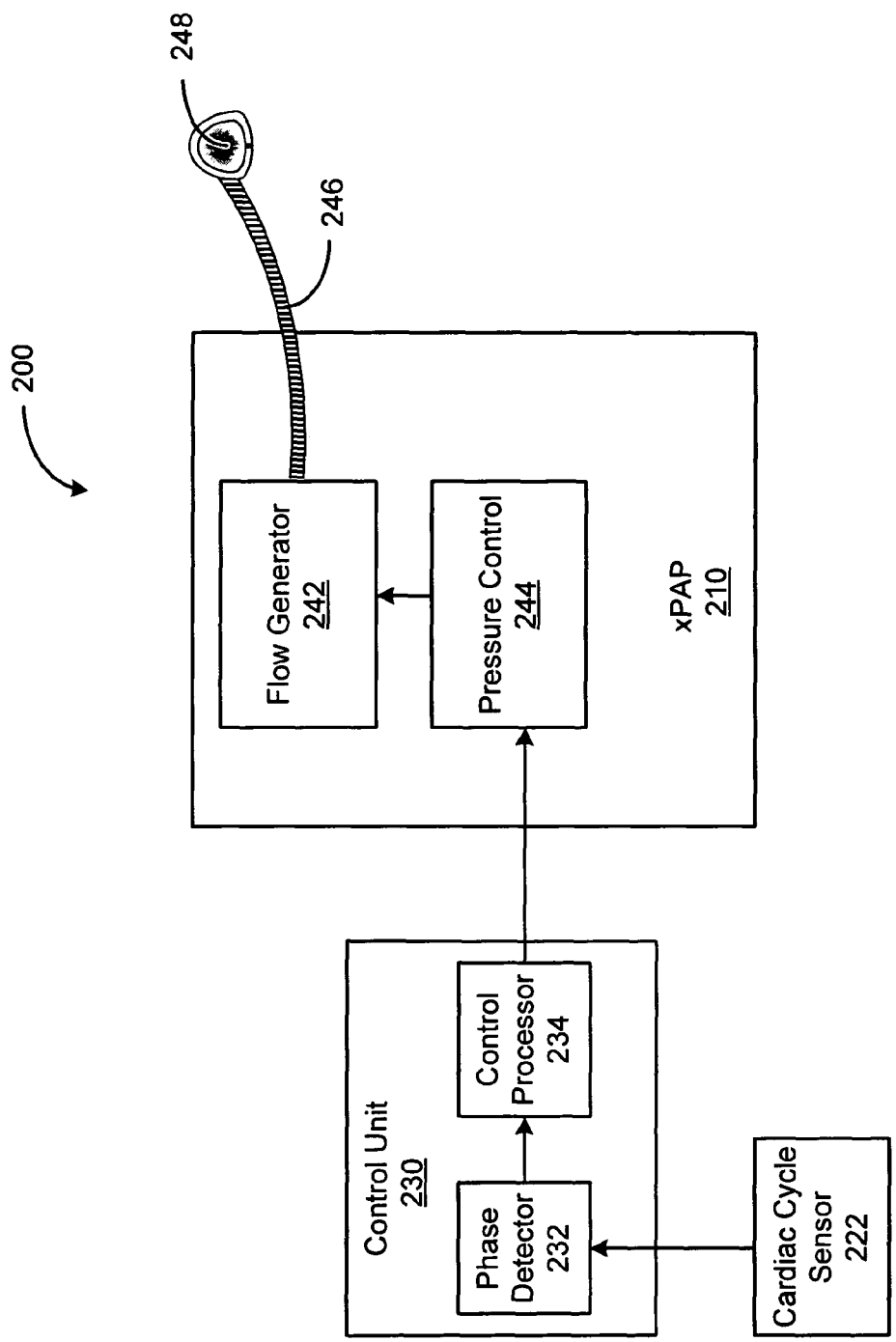
FIGS. 2A-2C are block diagrams illustrating systems that may be used to modulate intrathoracic pressure based on cardiac cycle phase in accordance with embodiments of the invention.
Figure 2B:
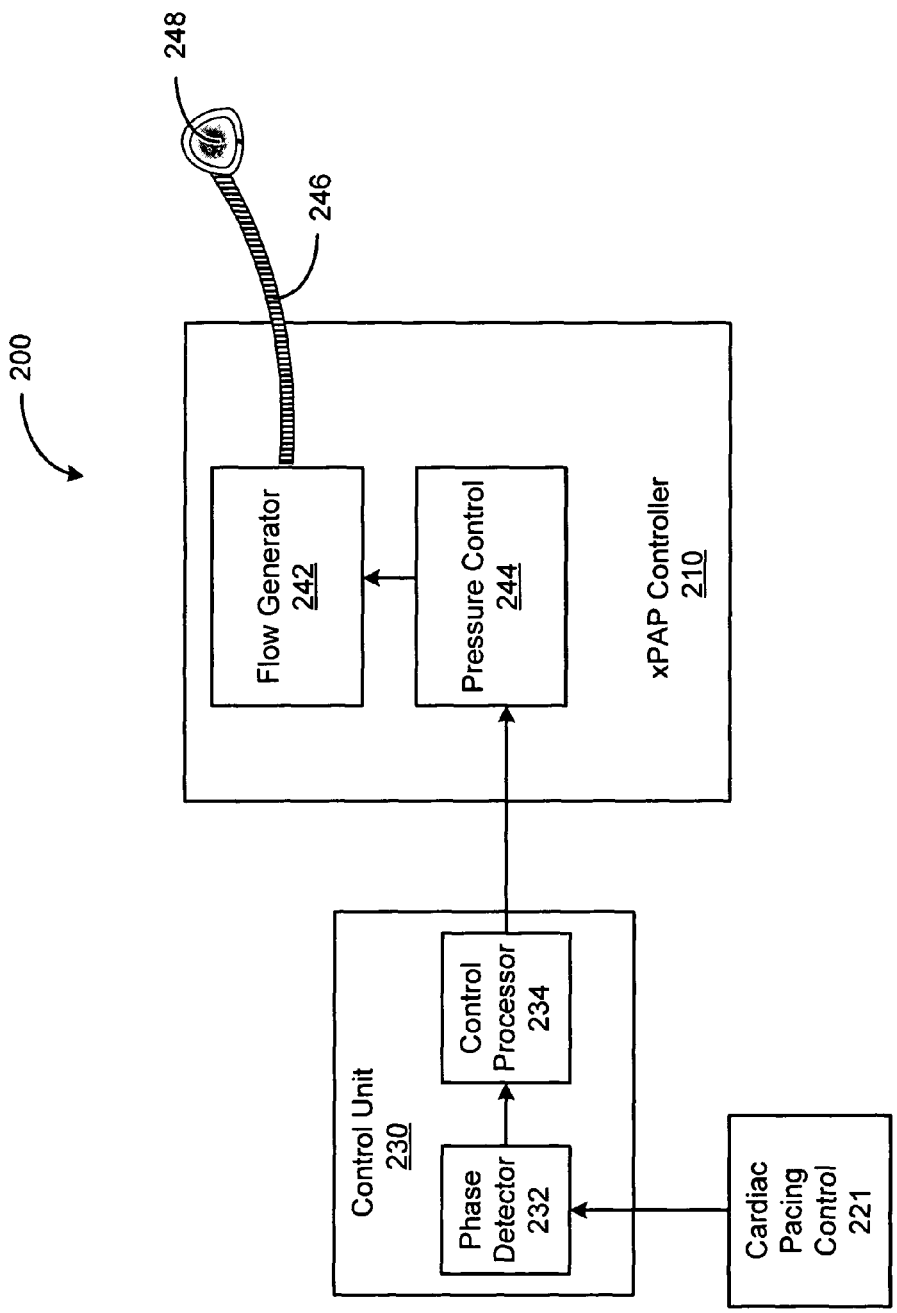
Figure 2C:
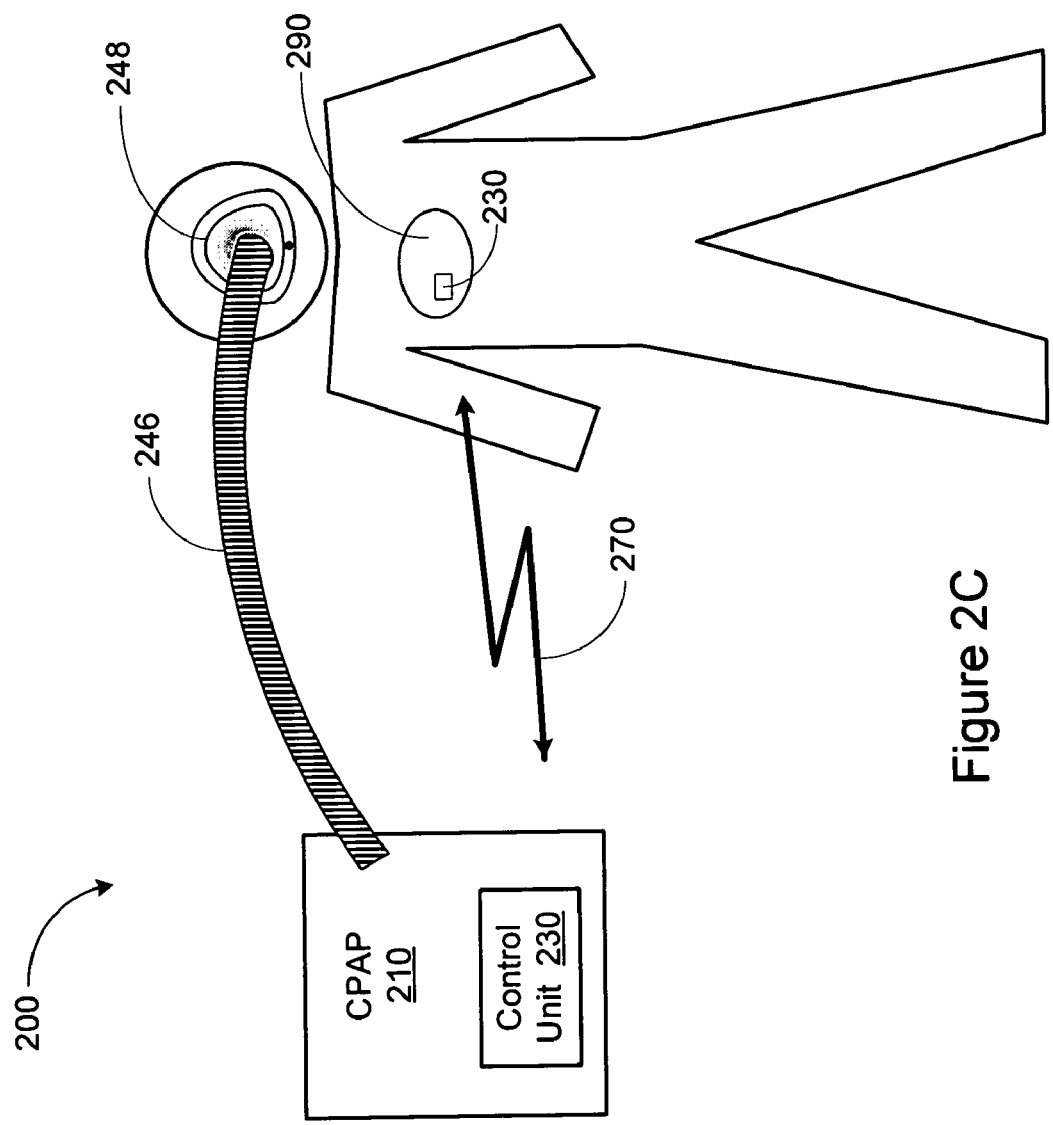

FIGS. 2A-2C are diagrams of systems employing a therapy controller that controls airway pressure delivered by the respiratory therapy device based on cardiac cycle phase. FIG. 2A is a block diagram illustrating a system 200 that may be used to modulate intrathoracic pressure based on cardiac cycle phase in accordance with embodiments of the invention. In this example, intrathoracic pressure is modulated by a positive airway pressure therapy system 200 comprising a positive airway pressure therapy controller unit 230 and airway pressure delivery components 248, 246. Respiratory therapy devices, including positive airway pressure (xPAP) devices may be used to treat disordered breathing, heart failure and/or other pulmonary disorders.

Positive airway pressure therapy is particularly useful in the treatment of disordered breathing. Disordered breathing may be caused by an obstructed airway or by derangement of the signals controlling respiration from the brain. Disordered breathing typically occurs while the patient is asleep, and is associated with excessive daytime sleepiness, systemic hypertension, increased risk of stroke, angina and myocardial infarction. Disordered breathing is related to congestive heart failure and can be particularly serious for patients concurrently suffering from cardiovascular deficiencies. Treatment for disordered breathing and/or heart failure may involve the used of an xPAP therapy system. An xPAP therapy system develops a positive air pressure that is delivered to the patient's airway, keeping the patient's airway open and reducing the severity and/or number of occurrences of disordered breathing due to airway obstruction. Reducing the number of occurrences of disordered breathing lessens the strain on the heart, thus providing therapy for heart failure.

Types of positive airway pressure devices may include, for example, continuous positive airway pressure (CPAP), bi-level positive airway pressure (bi-PAP), proportional positive airway pressure (PPAP), and/or auto-titrating positive airway pressure. Continuous positive airway pressure (CPAP) devices deliver a set air pressure to the patient. The pressure level for the individual patient may be determined during a titration study. Such a study may take place in a sleep lab, and involves determination of the optimum airway pressure by a sleep physician or other professional. The CPAP device pressure control is set to the determined level. When the patient uses the CPAP device, a substantially constant airway pressure level is maintained by the device.

Autotitrating PAP devices are similar to CPAP devices, however, the pressure controller for autotitration devices automatically determines the air pressure for the patient. Instead of maintaining a constant pressure, the autotitration PAP device evaluates sensor signals and the changing needs of the patient to deliver a variable positive airway pressure. Autotitrating PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others. Proportional PAP devices may gradually increase the therapy pressure, making it easier for patients to adjust to the therapy.

Other types of respiratory therapy devices may be used to develop airway pressure to treat disordered breathing and/or other respiratory diseases and disorders. Such device may include, for example, ventilators, gas or oxygen therapy devices, among others. Some devices, such as servo ventilation devices, provide airway pressure dependent on the respiration cycle stage. A servo ventilation device provides positive pressure on inhalation and negative pressure on exhalation. The term xPAP will be used herein as a generic term for any device that uses a form of positive airway pressure, whether continuous or otherwise.

The positive airway pressure (xPAP) device 210 of FIG. 2A, which is typically a bedside unit, delivers air or other gas through tubing 246 to a facial or nasal mask 248 worn by the patient. The airway pressure supplied by the xPAP device 210 acts as a pneumatic splint keeping the patient's airway open and reducing the severity and/or number of occurrences of disordered breathing due to airway obstruction.

The xPAP device 210 includes a flow generator 242 that pulls in air through a filter. The flow generator 242 is controlled by the pressure control circuitry 244 to deliver an appropriate air pressure to the patient. Air flows through tubing 246 coupled to the xPAP device 210 and is delivered to the patient's airway through a mask 248. In one example, the mask 248 may be a nasal mask covering only the patient's nose. In another example, the mask 248 covers the patient's nose and mouth.

The xPAP device 210 may include a communications unit for communicating with one or more separate devices, including patient-external and/or patient-internal monitoring, diagnostic and/or therapeutic devices. In one example, the xPAP device 210 may receive control signals for controlling delivery of the respiratory therapy from an implantable therapy or monitoring device. In another example, the xPAP device 210 may receive control signals for controlling delivery of the respiratory therapy from a patient management server or other computing device.

In one configuration, the xPAP unit 210 includes a control unit 230 that further contains a cardiac cycle sensor 222. The cardiac cycle sensor 222 measures a physiological parameter associated with the patient's cardiac cycle and sends cardiac cycle information to a phase detector 232. The phase detector 232 detects cardiac cycle phase based on the monitored physiological parameter. In one implementation, the cardiac cycle information may be determined from cardiac electrical activity detected using implantable electrogram (EGM) sensors or patient-external electrocardiogram (ECG) sensors. In other implementations the cardiac cycle information may be detected, for example, based on various parameters that may be sensed by the cardiac cycle sensor 222, including one or more of blood pressure, blood oxygen saturation, e.g., via pulse oximetry, thoracic motion, e.g., via thoracic electrical impedance, heart sounds, airway pressure modulation, and/or atrial tonometry.

Cardiac cycle phase may be determined by the timing of cardiac paces delivered to the patient. In one embodiment, illustrated in FIG. 2B, the phase detector determines cardiac cycle phase based on cardiac pacing information received from a pacemaker control unit 221. Cardiac pacing information may be used to determine cardiac cycle phase alternatively or in addition to sensed physiological parameters acquired by sensors as described in connection with FIG. 2A.

FIG. 2C illustrates a medical system for controlling respiratory therapy in accordance with embodiments of the invention. The system includes an external respiratory therapy controller unit 210 that delivers airway pressure through tubing 246 and mask 248. An implantable or patient-external cardiac cycle sensor is coupled a therapy controller 230 disposed within a housing of an implantable cardiac device 290. The implantable cardiac device 290 may comprise, for example, a cardiac therapy device, cardiac rhythm management (CRM) system, pacemaker, defibrillator, bi-ventricular pacemaker, intrathoracic cardiac sensing and/or stimulation (ITCS) system, cardiac resynchronizer, cardiac monitor, or other implantable cardiac device.

In one example, cardiac electrodes may be positioned in, on or about the heart in appropriate locations to sense the cardiac electrical activity of one or more heart chambers and/or to deliver pacing pulses to the heart. The cardiac electrodes may be coupled to the implantable cardiac device 290 through an intracardiac, intrathoracic, or subcutaneous lead system.

In one configuration, cardiac electrical activity is sensed by intracardiac EGM electrodes. Signals corresponding to the cardiac electrical activity are transmitted to a control unit 230 disposed within the implantable housing of the cardiac therapy or monitoring device 290. The control unit 230 evaluates the cardiac electrical signals to determine cardiac cycle phase. Control signals for controlling the airway pressure therapy are developed by the control unit 230 based on the sensed cardiac electrical activity. The control signals direct the respiratory therapy controller unit 210 to modulate therapy based on cardiac cycle phase.

In another configuration, the implantable cardiac device 290 comprises a cardiac rhythm management (CRM) system including a pacemaker that delivers cardiac pacing pulses to one or more heart chambers. The cardiac pacing pulses may be delivered to treat bradycardia, tachycardia and/or cardiac mechanical dysynchrony.

The pacing pulses produce contractions of the heart chambers that may be used to regulate and/or synchronize the heart contractions to enhance the pumping action of the heart. In this configuration, the cardiac cycle phase information may be determined from the timing of the cardiac paces. Cardiac pacing information, e.g., the timing of pacing pulses delivered to the heart chambers, may be provided to the therapy control unit 230 by the pacemaker of the CRM system 290. The cardiac pacing information is used by the therapy control unit 230 to develop control signals for controlling the respiratory therapy based on cardiac phase.

Figure 3A:
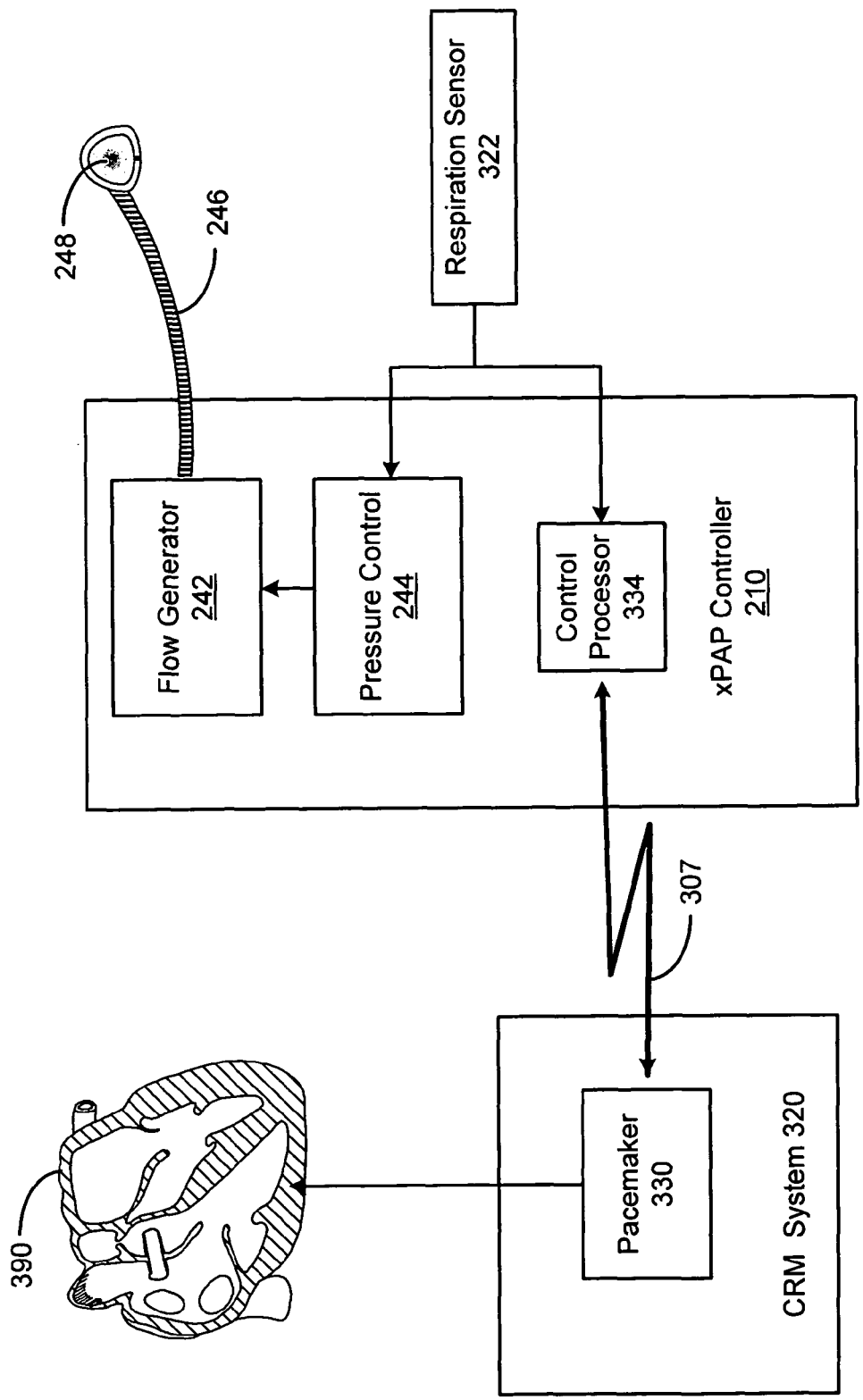
FIGS. 3A and 3B are block diagrams illustrating systems that may be used to modulate cardiac pacing based on respiration in accordance with embodiments of the invention.
Figure 3B:
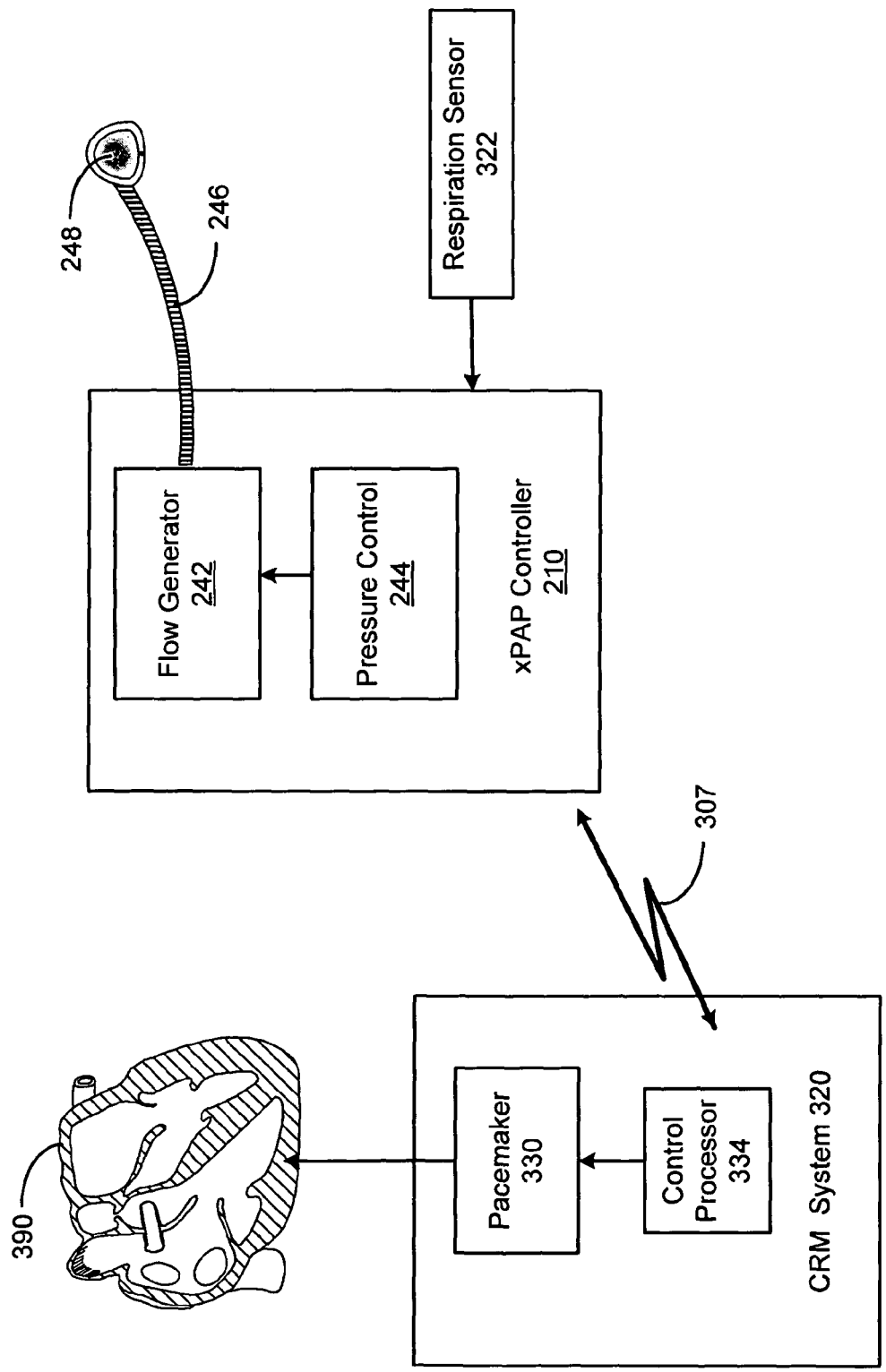

FIGS. 3A and 3B illustrate systems employing a therapy controller that develops a signal to control cardiac pacing based on respiration information acquired from sensors of a respiratory therapy system. In the block diagram of FIG. 3A, the control processor 334 is implemented as a component of the xPAP controller unit 210. The control processor 334 receives respiration information from a sensor 322 that senses a parameter modulated by respiration. In one example, the sensor 322 may comprise an airflow sensor of the respiratory therapy device. In other examples, the sensor 322 may comprise a motion sensor, such as a thoracic or abdominal motion sensor.

The control processor 334 utilizes the respiration information to develop a signal for controlling cardiac pacing. The control information is transmitted to the cardiac pulse generator 320 through a wireless communications link 307. Cardiac pacing pulses, delivered to the heart via the pacemaker 330 of the cardiac pulse generator 320, are modulated with respiration based on the control signals provided by the control processor 334.

FIG. 3B illustrates an embodiment wherein the control processor 334 is disposed within the implantable housing of the cardiac pulse generator 320. The control processor 334 receives respiration information acquired by the respiration sensor 322 of the respiratory therapy device. Respiration information is transmitted to the cardiac pulse generator 320 through a wireless communications link 307. The control processor develops a signal for controlling cardiac pacing based on the respiration information. Cardiac pacing pulses, delivered to the heart 390 via the pacemaker 330 of the cardiac pulse generator 320, are modulated by respiration.

Figure 4A:
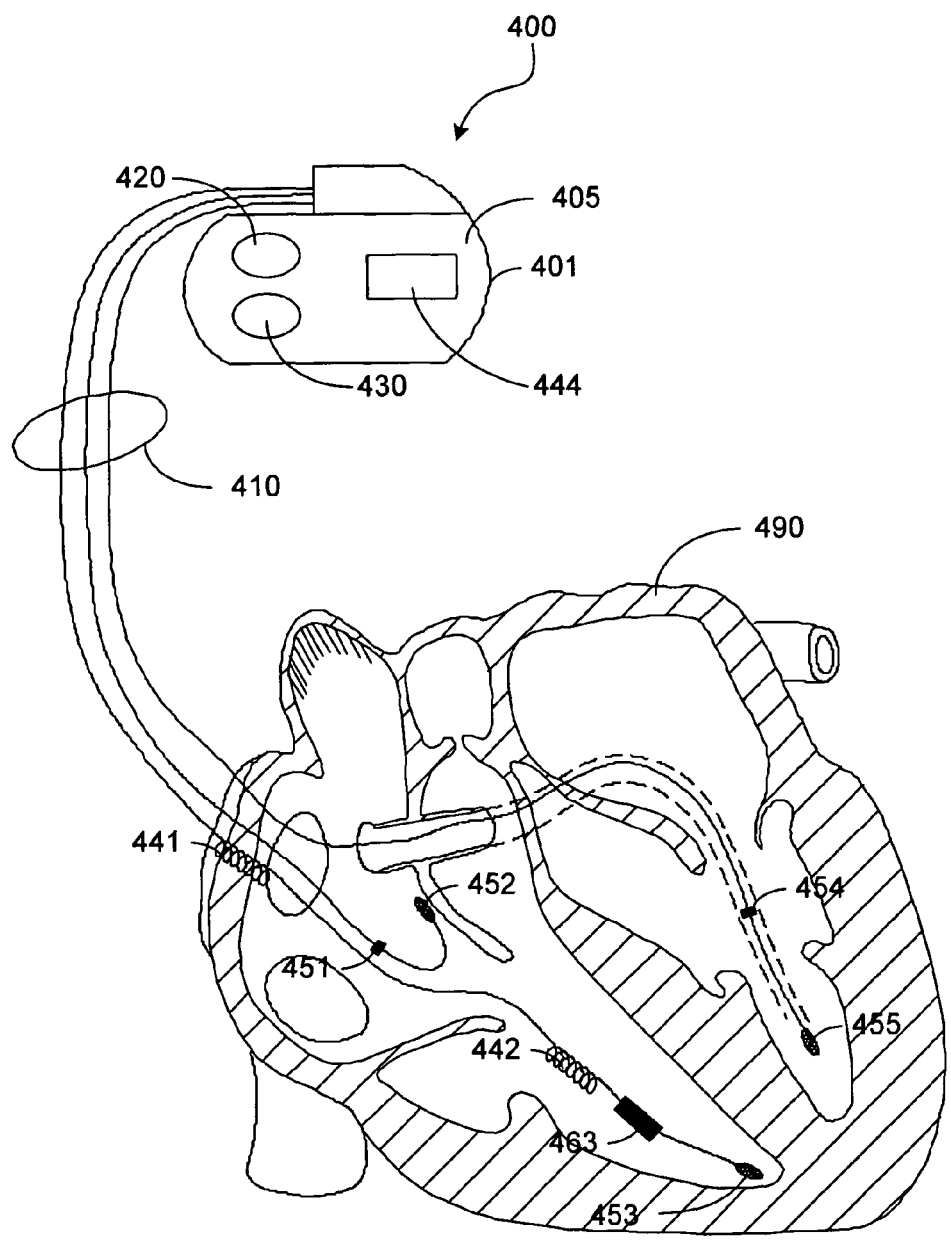
FIGS. 4A and 4B are partial views of implantable cardiac devices that may be used in connection with controlling respiratory therapy in accordance with embodiments of the invention.

FIG. 4A is a partial view of an implantable device that may include circuitry for controlling therapy to improve cardiopulmonary functioning in accordance with embodiments of the invention. The control unit 444 is configured as a component of a pulse generator 405 of a cardiac rhythm management device (CRM) 400. In some embodiments, the control unit 444, as described previously in connection with FIGS. 2A-2C, controls respiratory airway pressure based on cardiac cycle phase. In some embodiments, the control unit 444, as described in previously in connection with FIG. 3B, controls cardiac pacing based on respiration.

The implantable pulse generator 405 is electrically and physically coupled to an intracardiac lead system 410. The control unit 444 may be implemented in a variety of implantable monitoring, diagnostic, and/or therapeutic devices, such as an implantable cardiac monitoring device, pacemaker, defibrillator, cardioverter, cardiac resynchronizer, and the like.

Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 401 of the pulse generator 405 may optionally serve as a can electrode.

Communications circuitry is disposed within the housing 401, facilitating communication between the pulse generator 405 including the control unit 444 and an external device, such as a respiratory therapy device and/or advanced patient management system. The communications circuitry can also facilitate unidirectional or bidirectional communication with one or more implanted, external, cutaneous, or subcutaneous physiologic or non-physiologic sensors, patient-input devices and/or information systems.

The pulse generator 405 may optionally incorporate an accelerometer 420. The accelerometer may be disposed in or on the housing 401 of the pulse generator 405, or in other suitable locations. The accelerometer 420 may be used to detect heart sounds modulated by cardiac cycle.

The lead system 410 of the CRM 400 may incorporate a transthoracic impedance sensor that may be used to acquire the patient's respiration waveform, or other respiration-related information. The transthoracic impedance sensor may include, for example, one or more intracardiac electrodes 441, 442, 451-455, 463 positioned in one or more chambers of the heart 490. The intracardiac electrodes 441, 442, 451-455, 463 may be coupled to impedance drive/sense circuitry 430 positioned within the housing of the pulse generator 405.

In one implementation, impedance drive/sense circuitry 430 generates a current that flows through the tissue between an impedance drive electrode 451 and a can electrode on the housing 401 of the pulse generator 405. The voltage at an impedance sense electrode 452 relative to the can electrode changes as the patient's transthoracic impedance changes. The voltage signal developed between the impedance sense electrode 452 and the can electrode is detected by the impedance sense circuitry 430. Other locations and/or combinations of impedance sense and drive electrodes are also possible. The impedance signal may also be used to detect other physiological changes besides respiration that result in a change in impedance, including pulmonary edema, heart size, cardiac pump function, etc. The respiratory and/or pacemaker therapy may be altered on the basis of the patient's heart condition as sensed by impedance.

Figure 6:
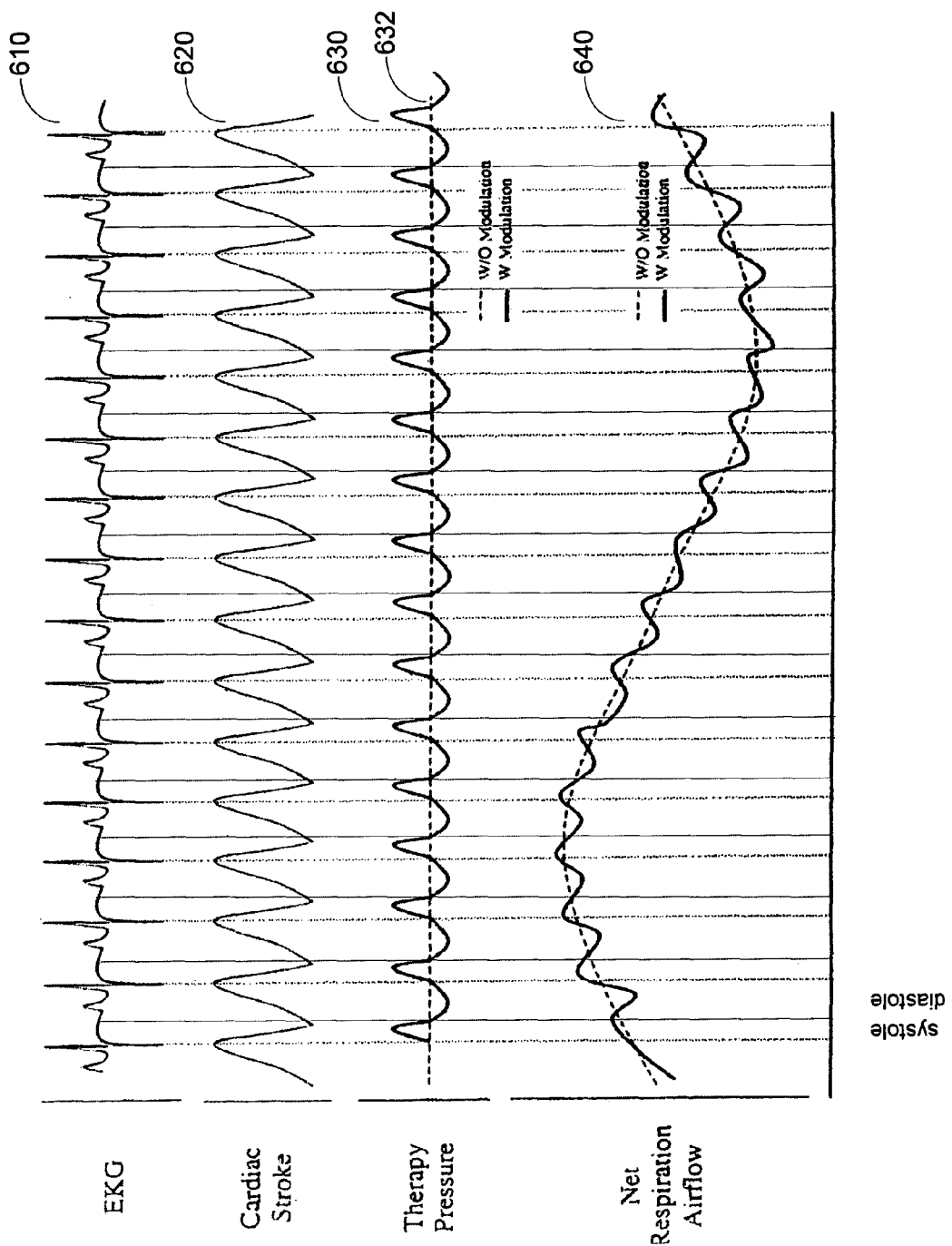
FIG. 6 illustrates modulation of therapy pressure during various cardiac cycles in accordance with embodiments of the invention.

The voltage signal developed at the impedance sense electrode 452 is proportional to the patient's transthoracic impedance. The transthoracic impedance signal may be used to generate a cardiac stroke waveform 620, as depicted in FIG. 6 or a respiration signal 102, as illustrated in FIG. 1.

The lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4A, may be used to sense cardiac electrical activity and/or to deliver pacing pulses to one or more chambers of the heart, including the left ventricle, the right ventricle, the left atrium and/or the right atrium. The lead system 410 may include one or more defibrillation electrodes 441, 442 for delivering defibrillation/cardioversion shocks to the heart. The electrodes 451-455, 441, 442 may be used to generate a cardiac electrical signal as illustrated in FIG. 5.

The pulse generator 405 may include circuitry for detecting cardiac arrhythmias and/or for controlling pacing or defibrillation therapy in the form of electrical stimulation pulses or shocks delivered to the heart through the lead system 410.

In some embodiments, the control unit 444 is used to develop a control signal for controlling airway pressure delivered to the patient based on cardiac cycle phase. In one example of respiration therapy control, the control unit 444 receives information from a sensor that produces a signal modulated by cardiac cycle phase. In one implementation, the sensor comprises an EGM sensor that produces a cardiac electrical activity signal. In another implementation, the sensor may comprise a transthoracic impedance sensor that produces a signal corresponding to a cardiac stroke. In yet a further implementation, the sensor may comprise an accelerometer or microphone that produces a signal corresponding to heart sound.

In another example of respiration therapy control, the control unit 444 receives cardiac pacing information and utilizes the cardiac pacing information to determine cardiac cycle phase. The control unit 444 produces a control signal that may be used to modulate airway pressure based on cardiac cycle phase.

A phase detector within the control unit 444 receives the sensor signal or cardiac pacing information and determines cardiac cycle phase. The cardiac cycle phase is used by the control processor 444 to implement control of respiratory therapy delivered to the patient based on cardiac cycle phase.

In some embodiments, the control unit is used to control cardiac pacing based on patient respiration. In one configuration, sensors of a respiratory therapy device acquire information related to patient respiration. For example, airflow sensors positioned on the mask or tubing of a respiratory therapy device may be used to determine patient respiration cycles. The respiration information is wirelessly transmitted from the respiration therapy device to the CRM device. The control unit 444 uses the respiration information for modulating cardiac pacing based on respiration. For example, the control unit may adjust a cardiac pacing rate with respiration to mimic normal respiratory sinus arrhythmia (RSA), for patients with degraded RSA functionality. Adjusting the cardiac pacing rate to mimic RSA my involve, for example, modulating the pacing rate above and below a base rate in synchrony with respiration cycles causing the patient's heart rate to vary as indicated in FIG. 1A.

Figure 4B:
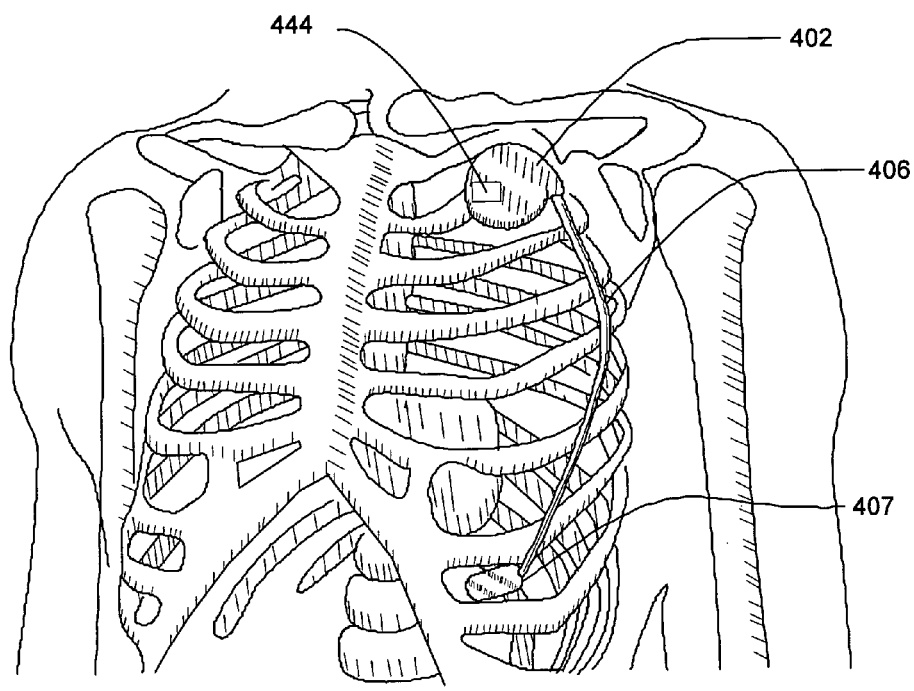

FIG. 4B is a diagram illustrating an implantable transthoracic cardiac device that may be used in connection with controlling therapy for improving cardiopulmonary function in accordance with embodiments of the invention. The implantable device illustrated in FIG. 4B is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

A control unit 444 for controlling respiratory or cardiac therapy may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 4B, a subcutaneous electrode assembly 407 can be positioned under the skin in the chest region and situated distal from the housing 402. The subcutaneous and, if applicable, housing electrode(s) can be positioned about the heart at various locations and orientations, such as at various anterior and/or posterior locations relative to the heart. The subcutaneous electrode assembly 407 is coupled to circuitry within the housing 402 via a lead assembly 406. One or more conductors (e.g., coils or cables) are provided within the lead assembly 406 and electrically couple the subcutaneous electrode assembly 407 with circuitry in the housing 402. One or more sense, sense/pace or defibrillation electrodes can be situated on the elongated structure of the electrode support, the housing 402, and/or the distal electrode assembly (shown as subcutaneous electrode assembly 407 in FIG. 4B).

It is noted that the electrode and the lead assemblies 407, 406 can be configured to assume a variety of shapes. For example, the lead assembly 406 can have a wedge, chevron, flattened oval, or a ribbon shape, and the subcutaneous electrode assembly 407 can comprise a number of spaced electrodes, such as an array or band of electrodes. Moreover, two or more subcutaneous electrode assemblies 407 can be mounted to multiple electrode support assemblies 406 to achieve a desired spaced relationship amongst subcutaneous electrode assemblies 407.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203, 348; 5,230,337; 5,360,442; 5,366,496; 5,397,342; 5,391,200; 5,545,202; 5,603,732; and 5,916,243 and commonly owned U.S. Patent Application Ser. No. 60/462,272, filed Apr. 11, 2003 and now abandoned, U.S. Patent Application Publication US 2004/0230229 (Lovett et al.), U.S. Patent Application Publication US 2004/0230230 (Lindstrom et al.), U.S. Patent Application Publication US 2004/0215258 (Lovett et al.), and U.S. Patent Application Publication US 2004/0215240 (Lovett et al.), which are incorporated herein by reference.

In one implementation, the ITCS device may include an impedance sensor configured to sense the patient's transthoracic impedance. The impedance sensor may include the impedance drive/sense circuitry incorporated with the housing 402 of the ITCS device and coupled to impedance electrodes positioned on the can or at other locations of the ITCS device, such as on the subcutaneous electrode assembly 407 and/or lead assembly 406. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

The housing of the ITCS device may incorporate components of a control unit 444, including a phase detector and a control processor. In embodiments where airway pressure is controlled based on cardiac cycle phase, the control unit 444 may be coupled to one or more sensors configured to sense cardiac electrical activity, cardiac stroke, and/or heart sounds for determining cardiac cycle phase. Alternatively or additionally, the control unit may receive cardiac pacing information from circuitry controlling the pacing function of the ITCS or another cardiac therapy device. The control unit may be communicatively coupled to the respiratory therapy device through a wireless communication link.

In some embodiments, the control unit 444 may receive respiration information acquired by sensors of a respiration therapy device. The control unit 444 may use the respiration information to control cardiac pacing. The cardiac pacing rate may be modulated based on respiration to mimic RSA behavior.

Communications circuitry is disposed within the housing 402 for facilitating communication between the ITCS device, including the control unit 444, and an external device, such as a portable or bed-side respiratory therapy device, advanced patient management server or external programmer, for example. The communications circuitry can also facilitate unidirectional or bidirectional communication with one or more external, cutaneous, or subcutaneous physiologic or non-physiologic sensors.

FIGS. 5A and 5B are flowcharts of methods that may be implemented by the systems depicted herein to adjust intrathoracic pressure based on cardiac cycle phase in accordance with embodiments of the invention. As illustrated in FIG. 5A, a method involves determining 510 cardiac cycle phase by sensing a physiological parameter associated with a cardiac cycle. Control of airway pressure is based on 520 the cardiac cycle phase. In one embodiment, the physiological parameter used to determine cardiac cycle phase comprises cardiac electrical activity which may be sensed using an EGM sensor. In other implementations, the cardiac cycle phase may be determined based on a cardiac stroke signal acquired, via a transthoracic impedance sensor or a heart sound signal acquired via a microphone or an accelerometer.

The method depicted by the flowchart of FIG. 5B involves sensing 530 a physiological parameter indicative of cardiac phase. During systole 540, the therapy pressure is increased 550, e.g., above a baseline pressure. During diastole 560, the therapy pressure is decreased 570.

FIG. 5C illustrates a method of controlling cardiac pacing in accordance with embodiments of the invention. A parameter associated with respiration is sensed 580 using a sensor of a respiratory therapy device. For example, the respiratory therapy device may comprise a positive airway pressure device, gas therapy device, nebulizer, ventilator, or other device that delivers respiratory therapy to the patient and includes a sensing system configured to sense a parameter that is modulated by respiration. In one example, the respiratory therapy device may include or be coupled to a blood pressure sensor. In another example, the respiratory therapy device may include or be coupled to an air flow sensor.

Cardiac pacing is controlled based on the sensed parameter associated with respiration. For example, the cardiac pacing rate may be modulated above and below a base rate to mimic RSA. Modulating the cardiac pacing rate with respiration restores normal respiratory sinus arrhythmia in patients who have lost this functionality. Such therapy is particularly useful for patient's suffering from cardiopulmonary diseases such as congestive heart failure. In one embodiment a phase shift is imposed between the respiratory phase and the cardiac phase produced by the cardiac pacing to more closely mimic RSA.

FIG. 6 graphically illustrates modulation of respiratory therapy pressure based on cardiac phase in accordance with embodiments of the invention. FIG. 6 compares graphs of an ECG signal 610, cardiac stroke signal from an implanted impedance sensor 620, therapy pressure 630, and net respiration flow 640 (as measured into the patient). The net respiration flow 640 illustrates the patient's respiration cycle modulated by the therapy pressure delivered to the patient. As shown in FIG. 6, the therapy pressure 630 delivered by the respiratory therapy device is modulated by the phase of the cardiac cycle. The phase of the cardiac cycle may be determined based on the ECG signal 610 and/or the cardiac impedance stroke signal 620. Thus, the therapy pressure is increased above its otherwise static positive value 632 during cardiac systole. The increased thoracic pressure reinforces the cardiac contraction and thus reduces cardiac afterload. During cardiac diastole, the respiratory therapy pressure is decreased from its otherwise static positive value 632. Although reduced, the therapy pressure is still positive in this embodiment. However, in other embodiments the applied pressure may be zero or negative during cardiac diastole. The reduced ventilation pressure during cardiac diastole assists the heart in filling and thereby increases preload. The control unit may anticipate the cardiac cycle phase based on recent cardiac cycle history.

Using the respiratory pressure to reinforce the pumping action of the heart results in increased cardiac output with decreased expenditure of myocardial energy output. Modulation of the therapy pressure based on cardiac cycle phase may be used to improve cardiac functioning during delivery of respiratory therapy. The respiratory therapy may be prescribed to the patient for nightly use to alleviate or reduce episodes of sleep disordered breathing, such as sleep apnea and/or other pulmonary disorders. The addition of therapy pressure modulation matched to cardiac cycle phase provides an improvement of cardiac function and may positively impact long-term patient outcomes. Modulation of respiratory therapy pressure based on cardiac cycle phase may contribute to slowing, halting, or reversing congestive heart failure and/or hypertension.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

What is claimed is:

1. A method for delivering airway pressure to a patient, comprising:
    providing a patient-implantable cardiac rhythm monitoring system adapted to electrically couple to the patient's heart and to communicate with a patient-external respiratory therapy device;
    determining cardiac cycle phase using the cardiac rhythm monitoring system, including determining if the cardiac cycle phase is systole or diastole based on one or more of (a) implantably sensing a parameter indicative of the cardiac cycle phase, and (b) determining delivery of a cardiac pacing pulse; and
    controlling the airway pressure delivered by the patient-external respiratory therapy device in synchrony with the cardiac cycle phase, wherein controlling the airway pressure is performed at least in part implantably.

2. The method of claim 1, wherein sensing the parameter comprises sensing oxygen saturation.

3. The method of claim 1, wherein sensing the parameter comprises sensing blood pressure.

4. The method of claim 1, wherein sensing the parameter comprises sensing cardiac electrical activity.

5. The method of claim 1, wherein sensing the parameter comprises sensing a parameter associated with cardiac motion.

6. The method of claim 5, wherein sensing the parameter associated with cardiac motion comprises sensing transthoracic impedance.

7. The method of claim 5, wherein sensing the parameter associated with cardiac motion comprises sensing heart sounds.

8. The method of claim 1, wherein implantably controlling the airway pressure comprises matching intrathoracic pressure with cardiac cycle phase.

9. The method of claim 1, wherein implantably controlling the airway pressure comprises:
    delivering a first airway pressure during a first cardiac cycle phase; and
    delivering a second airway pressure during a second cardiac cycle phase.

10. The method of claim 1, wherein implantably controlling the airway pressure comprises:
    modulating airway pressure above a baseline pressure during cardiac systole; and
    modulating airway pressure below a baseline pressure during cardiac diastole.

11. The method of claim 1, wherein:
    determining the cardiac cycle phase comprises anticipating the cardiac cycle phase; and
    implantably controlling the airway pressure comprises controlling the airway pressure based on the anticipated cardiac cycle phase.

12. The method of claim 11, wherein anticipating the cardiac cycle comprises anticipating the cardiac cycle based on recent cardiac cycle history.

13. The method of claim 1, wherein implantably controlling the airway pressure comprises implantably controlling airway pressure to improve at least one of ventricular preload or ventricular afterload.

14. The method of claim 1, wherein implantably controlling the airway pressure comprises implantably controlling the airway pressure to enhance cardiac pumping action.

15. A therapy control system, comprising:
    a patient-implantable pulse generator configured to deliver cardiac pacing pulses to a patient's heart based on cardiac pacing information;
    a patient-implantable cardiac rhythm monitoring system adapted to electrically couple to the patient's heart and to communicate with a patient-external respiratory therapy device, the cardiac rhythm monitoring system including a detector system including a sensor configured to implantably sense a parameter associated with cardiac cycle phase, the detector system being configured to determine if the cardiac cycle phase is systole or diastole based on one or more of the sensed parameter and the cardiac pacing information; and
    a control unit coupled to the detector system and configured to control airway pressure delivered by the patient-external respiratory therapy device in synchrony with the cardiac cycle phase, wherein the control unit includes at least one implantable component.

16. The system of claim 15, further comprising the patient-external respiratory therapy unit which is configured to deliver an external respiratory therapy to the patient, wherein the implantable control unit is configured to control the delivery of the external respiratory therapy based on the cardiac cycle phase.

17. The system of claim 15, wherein the implantable control unit is configured to match intrathoracic pressure with cardiac cycle.

18. The system of claim 15, wherein the implantable control unit is configured to deliver a first airway pressure during a first cardiac cycle phase and to deliver a second airway pressure during a second cardiac cycle phase.

19. The system of claim 15, wherein the implantable control unit is configured to modulate airway pressure above a baseline pressure during cardiac systole and to modulate airway pressure below a baseline pressure during cardiac diastole.

20. The system of claim 15, wherein:
    the detector system is configured to anticipate the cardiac cycle phase; and
    the implantable control unit is configured to control the airway pressure based on the anticipated cardiac cycle phase.

21. The system of claim 20, wherein the detector system is configured to store cardiac cycle history and to anticipate the cardiac cycle phase based on the cardiac cycle history.

22. The system of claim 15, wherein the implantable control unit is configured to control the airway pressure comprises to improve at least one of ventricular preload or ventricular afterload.

23. A system for controlling delivery of airway pressure to a patient, comprising:

a patient-implantable pulse generator configured to deliver cardiac pacing pulses to a patient's heart based on cardiac pacing information;

patient-implantable cardiac rhythm monitoring system means for electrically coupling to the patient's heart and for communicating with a patient-external respiratory therapy device;

means for determining cardiac cycle phase using the cardiac rhythm monitoring system means, the determining means including means for implantably sensing a parameter indicative of cardiac cycle phase, wherein the determining means determines if the cardiac cycle phase is systole or diastole based on one or more of the parameter and the cardiac pacing information: and means for implantably controlling the airway pressure delivered by the patient-external respiratory therapy device in synchrony with the cardiac cycle phase.

\* \* \* \* \*